United States Patent
Kawata et al.

(10) Patent No.: US 10,595,798 B2
(45) Date of Patent: Mar. 24, 2020

(54) DETECTION APPARATUS AND DETECTION METHOD

(71) Applicant: Canon Medical Systems Corporation, Otawara-shi (JP)

(72) Inventors: Go Kawata, Nagareyama (JP); Keita Sasaki, Yokohama (JP); Rei Hasegawa, Yokohama (JP)

(73) Assignee: Canon Medical Systems Corporation, Otawara-shi (JP)

( * ) Notice: Subject to any disclaimer, the term of this patent is extended or adjusted under 35 U.S.C. 154(b) by 248 days.

(21) Appl. No.: 15/683,819

(22) Filed: Aug. 23, 2017

(65) Prior Publication Data

US 2018/0206804 A1    Jul. 26, 2018

(30) Foreign Application Priority Data

Jan. 24, 2017    (JP) .................. 2017-010504

(51) Int. Cl.
| | | |
|---|---|---|
| *A61B 6/00* | (2006.01) | |
| *G01T 1/17* | (2006.01) | |
| *G01T 1/18* | (2006.01) | |
| *G01T 1/20* | (2006.01) | |
| *G01T 1/29* | (2006.01) | |

(52) U.S. Cl.
CPC .......... *A61B 6/4233* (2013.01); *A61B 6/4241* (2013.01); *G01T 1/17* (2013.01); *G01T 1/18* (2013.01); *G01T 1/20* (2013.01); *G01T 1/2018* (2013.01); *G01T 1/2985* (2013.01)

(58) Field of Classification Search
CPC ... A61B 6/4233; A61B 6/4241; G01T 1/2018; G01T 1/17; G01T 1/20; G01T 1/18; G01T 1/2985

USPC .................................................... 250/336.1
See application file for complete search history.

(56) References Cited

U.S. PATENT DOCUMENTS

| | | | |
|---|---|---|---|
| 7,190,917 B2 | 3/2007 | Suzumi et al. | |
| 7,606,347 B2 | 10/2009 | Tkaczyk et al. | |
| 9,423,511 B2 | 8/2016 | Frach et al. | |
| 2013/0009267 A1* | 1/2013 | Henseler | G01T 1/248 257/443 |
| 2016/0011323 A1* | 1/2016 | Sasaki | G01J 1/44 250/370.08 |
| 2017/0086762 A1 | 3/2017 | Kawata et al. | |

FOREIGN PATENT DOCUMENTS

| | | |
|---|---|---|
| JP | 2005-107237 | 4/2005 |
| JP | 2010-527021 | 8/2010 |
| JP | 5215722 | 6/2013 |
| JP | 2014-241543 | 12/2014 |
| JP | 2017-067634 | 4/2017 |

\* cited by examiner

*Primary Examiner* — David P Porta
*Assistant Examiner* — Meenakshi S Sahu
(74) *Attorney, Agent, or Firm* — Oblon, McClelland, Maier & Neustadt, L.L.P.

(57) ABSTRACT

A detection apparatus according to an embodiment includes first detectors, a first electrode, second detectors and a second electrode. The first detectors detect a photon. The first electrode is electrically connected to each of the first detectors. The second detectors detect a photon. The second electrode is electrically connected to each of the second detectors. The number of first detectors is less than the number of second detectors.

13 Claims, 5 Drawing Sheets

DETECTION APPARATUS AND DETECTION METHOD

CROSS-REFERENCE TO RELATED APPLICATIONS

This application is based upon and claims the benefit of priority from Japanese Patent Application No. 2017-010504, filed on Jan. 24, 2017; the entire contents of which are incorporated herein by reference.

FIELD

Embodiments of the present invention relate to a detection apparatus and a detection method.

BACKGROUND

In a radiation detection apparatus, a measuring unit that guarantees the linearity of radiation detection is desired irrespective of a radiation dose. In a detection method using a photon counting method of measuring radiation as a photon, a counting loss due to pile-up becomes a problem at high photon number.

DETAILED DESCRIPTION

Figure 1A:
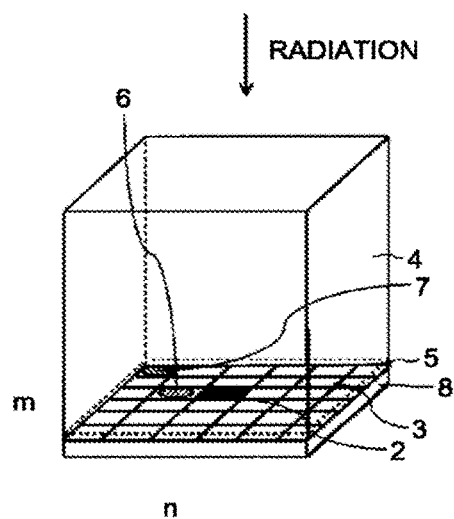
FIGS. 1A to 1D illustrate a detection apparatus according to a first embodiment.

A detection apparatus according to an embodiment includes first detectors, a first electrode, second detectors and a second electrode. The first detectors detect a photon. The first electrode is electrically connected to each of the first detectors. The second detectors detect a photon. The second electrode is electrically connected to each of the second detectors. The number of first detectors is less than the number of second detectors.

Embodiments of the present invention will be described below with reference to the drawings. A component with a similar reference numeral indicates a similar component. It should be noted that the drawings are schematic or conceptual, a relationship between the thickness and the width of each part, the ratio coefficient of the size between parts, and the like are not necessarily the same as the actual ones. Even in the case of expressing the same part, there is a case where dimensions and proportionality coefficients of the parts are different from each other depending on the drawing.

First Embodiment

FIG. 1A illustrates an external view of a detection apparatus according to a first embodiment.

The detection apparatus 1 according to the first embodiment includes a scintillator 4, an adhesive layer 5, a substrate 8, reading units 9 and 10, and a processing unit 11. The substrate 8 has one first detector 2, a plurality of second detectors 3, a first electrode unit 6, and a second electrode unit 7.

In FIG. 1A, the reading units 9 and 10 and the processing unit 11 are not illustrated and their description will be described later.

The first detector 2 and the second detector 3 are formed, for example, in the substrate 8.

A radiation is incident on the detection apparatus 1 from the direction of the arrow. The scintillator 4 converts the radiation and emits it as visible light. At that time, the number of visible light photons proportional to the energy of the radiation is emitted. The photon emitted from the scintillator 4 is incident on the first detector 2 and the second detector 3 provided on the substrate 8, and is converted into an electric signal. Here, the photon-transmitting adhesive layer 5 may be provided between the substrate 8 having the first detector 2 and the second detector 3 and the scintillator 4.

Both of the first detector 2 and the second detector 3 are rectangular plane detectors, and have substantially the same size as the detector on the light receiving surface. The first detector 2 and the second detector 3 are laid in an array on the substrate 8 to form a plurality of detectors.

In the embodiment within the present specification, the light receiving surface is a plane substantially perpendicular to the incident direction of radiation, and a plurality of plane detectors are two-dimensionally arranged along a first direction and a second direction substantially orthogonal to the first direction.

In the detection apparatus according to the present embodiment, one first detector 2 is used, and the second detectors 3 are used except for the first detector 2. It is preferable that the first detector 2 is provided substantially at the center of the light receiving surfaces of the plurality of two-dimensionally arrayed plane detectors. That is, it can be said that the first detector 2 is positioned at the center of the detection apparatus according to the present embodiment on the light receiving surface. The first detector 2 and the second detector 3 are, for example, photon counting type detectors.

As a material of the scintillator 4, there are thallium activated cesium iodide (CsI(Tl)), thallium activated sodium iodide (NaI(Tl)), and LYSO(Lu2(1−x)Y2x(SiO4)O). The range of x in the composition formula of LYSO is $0.001 \leq x \leq 0.5$. The adhesive layer 5 transmits a photon from the scintillator 4. As a material of the adhesive layer 5, an epoxy material or the like is used. As the substrate 8, a combination of an insulator which a photon passes and a photo-electron converting material, such as $SiO_2$ and silicon diode, is used.

Regardless of the example in FIG. 1A, the light receiving areas of the plurality of two-dimensionally m×n arrayed plane detectors (an integer m is the number of detectors in a first direction and an integer n is the number of detectors in a second direction) of the first detector 2 and the second detector 3 may be different. The light receiving area refers to an area of a light receiving element on the light receiving surface, and the light receiving element is an element that receives a photon and converts the photon into an electric signal. For example, the light receiving area of the first detector 2 may be twice, four times or the like the light receiving area of the second detector 3.

Figure 1C:
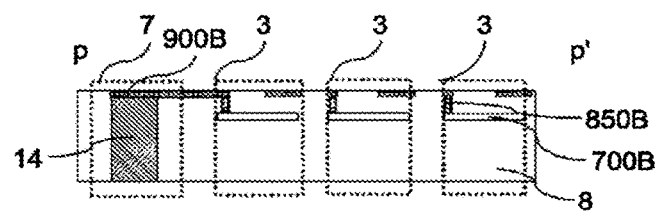
Figure 1B:
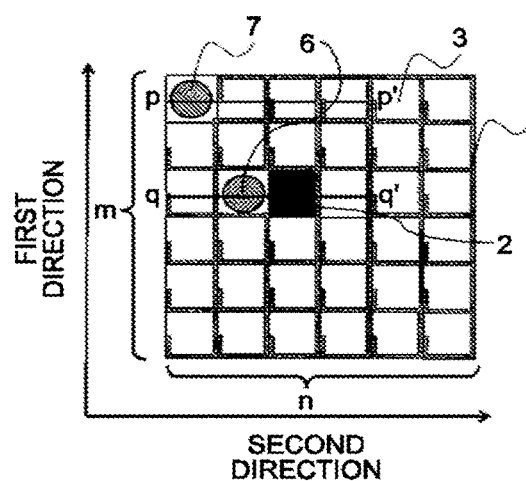

FIG. 1B illustrates a plan view of the detection apparatus 1 in which the scintillator 4 and the adhesive layer 5 are omitted as viewed from the direction of incidence of radiation.

As illustrated in FIG. 1B, the first detector 2 and the second detector 3 are two-dimensionally arranged in an array on the light receiving surface of the substrate 8. For example, two of the plurality of second detectors 3 two-dimensionally arranged are replaced with electrode units 6 and 7. The first wiring 900B is provided to bundle a signal obtained when the plurality of second detectors 3 detect a photon to transmit the signal to the electrode unit 7, and is connected to the electrode unit 7 through the edge of the second detector 3.

The first electrode unit 6 is configured to output an electric signal from the first detector 2 to the processing unit 11 described later. The first electrode unit 6 is provided in the vicinity (also referred to as adjacent) of the first detector 2 in the second direction. In the two-dimensionally laid detectors, the second electrode unit 7 is provided at one of the four corners as viewed from the direction of incidence of radiation. The second electrode unit 7 is configured to output electric signals from the plurality of second detectors 3 to the processing unit 11.

Regardless of the example in FIG. 1B, the first electrode unit 6 and the second electrode unit 7 may overlap on the detector and the light receiving surface of the substrate 8. That is, it is not necessary to replace the plurality of laid detectors with the first electrode unit 6 and the second electrode unit 7. In addition, each of the first electrode unit 6 and the second electrode unit 7 may not be one but each may be plural. The second electrode unit 7 may not be provided at the four corners, and may be replaced with any one of the plurality of second detectors 3.

FIG. 1C is a cross-sectional view obtained by cutting p-p' in FIG. 1B in a first direction.

Figure 1D:
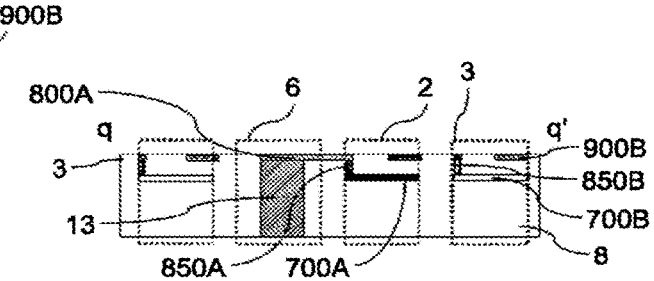

FIG. 1D is a cross-sectional view obtained by cutting q-q' in FIG. 1B in a first direction.

As illustrated in FIG. 1C, the second detector 3 includes a light receiving element 700B that receives a photon and converts the photon into an electric signal, a second wiring 850B that outputs the electric signal from the light receiving element 700B to a first wiring 900B, and the first wiring 900B that outputs the electric signal output to the second wiring 850B to the second electrode unit 7. The second electrode unit 7 includes a second electrode 14.

The second wiring 850B and the first wiring 900B around the light receiving element 700B are regions that cannot transmit a photon, and thus are arranged at the end of the light receiving element 700B in the second direction. The first wiring 900B is connected to the second wiring 850B through the edge of the second detector 3 so as not to narrow the light receiving region of the light receiving element 700B. In addition, the first wiring 900B passes through the edges of the adjacent first detector 2 and second detector 3 and is connected to the second electrode unit 7. Each of the first wirings 900B of the plurality of second detectors 3 passes along the surface on the light receiving surface side, passes through the edges of the plurality of second detectors 3, and is finally connected to the second electrode 14 across one end (upper end) of the second electrode unit 7. As a result, all the electric signals of the second detector 3 are output to the second electrode unit 7. An insulator such as SiO$_2$ that allows photons to pass therethrough is provided between the light receiving element 700B and the first wiring 900B and the second wiring 850B so as not to cause accidental short circuit with the surrounding wiring.

As illustrated in FIG. 1D, the first detector 2 includes a light receiving element 700A that receives a photon and converts the photon into an electric signal, a second wiring 850A that outputs the electric signal from the light receiving element 700A to a first wiring 800A, and the first wiring 800A that outputs the electric signal output to the second wiring 850A to the first electrode unit 6.

The first electrode unit 6 includes a first electrode unit 13.

The first detector 2 and the first electrode unit 13 are connected by the first wiring 800A. In addition, the first wiring 800A is formed to extend across the upper ends of the first detector 2 and the first electrode unit 13.

An insulator such as SiO$_2$ that allows photons to pass therethrough is provided between the light receiving element 700A and the first wiring 800A and the second wiring 850A so as not to cause accidental short circuit with the surrounding wiring.

The first wiring 800A and the second wiring 850A are regions that cannot transmit photons, and thus are arranged at the end while avoiding the light receiving element 700A as much as possible.

In FIG. 1D, the second detector 3 is the same as FIG. 1C, so that its explanation will be omitted.

In the examples of FIGS. 1C and 1D, the size of the light receiving surface of the light receiving elements 700A and 700B is 1 mm×1 mm.

Figure 2:
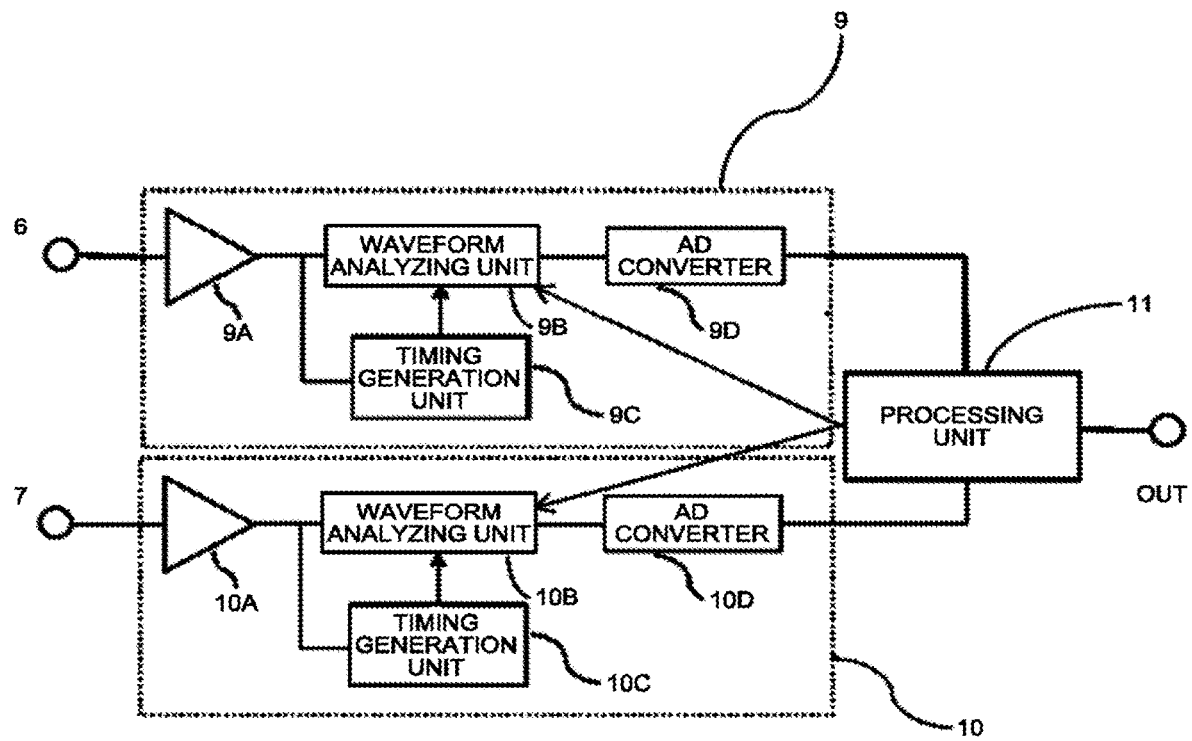
FIG. 2 illustrates a route to process a signal obtained by a detector.

FIG. 2 illustrates a route to process a signal obtained by the detector.

The reading unit 9 receives an electric signal (analog waveform) obtained from the first detector 2 via the first electrode unit 6. The reading unit 10 receives an electric signals collected from the plurality of second detectors 3 via the second electrode unit 7. Each of the electric signals is converted into a digital signal by the reading units 9 and 10, and is output to the processing unit 11.

An ASIC (Application Specific Integrated Circuit) or the like is used for the reading units 9 and 10.

The reading unit 9 includes an amplifying unit 9A that amplifies an electric signal, a waveform analyzing unit 9B that analyzes the pulse height of the amplified electrical signal, a timing generation unit 9C that transmits to the waveform analyzing unit 9B that the electric signal is output from the amplifying unit 9A, and an AD converter 9D that converts an electric signal into a digital signal.

The waveform analyzing unit 9B, the timing generation unit 9C, and the processing unit 11 may be operated by one control device (circuit). This control device detects an electric signal output from the first electrode unit 6. The first electrode unit 6 outputs an electric signal having a pulse height proportional to the energy of a radiation photon. The electric signal is a pulse signal. The pulse signal is amplified by the amplifying unit 9A and analyzed by the waveform analyzing unit 9B. The timing generation unit 9C notifies the waveform analyzing unit 9B that a pulse signal is output. The pulse signal read out by the waveform analyzing unit 9B is converted into a digital signal by the AD converter 9D and output to the processing unit 11.

The reading unit 10 includes an amplifying unit 10A that amplifies an electric signal, a waveform analyzing unit 10B that analyzes the pulse height of the amplified electrical signal, a timing generation unit 10C that transmits to the waveform analyzing unit 10B that the electric signal is output from the amplifying unit 10A, and an AD converter 10D that converts an electric signal into a digital signal.

The waveform analyzing unit 10B, the timing generation unit 10C, and the processing unit 11 may be operated by one control device (circuit). This control device detects an electric signal from the second electrode unit 7. The second electrode unit 7 outputs an electric signal having a pulse height proportional to the energy of a radiation photon. The electric signal is a pulse signal. The pulse signal is amplified by the amplifying unit 10A and analyzed by the waveform analyzing unit 10B. The timing generation unit 10C notifies the waveform analyzing unit 10B that a pulse signal is output. The pulse signal read out by the waveform analyzing unit 10B is converted into a digital signal by the AD converter 10D and output to the processing unit 11.

The processing unit 11 sets a threshold value used for processing in the waveform analyzing unit 9B and the waveform analyzing unit 10B. Further, the processing unit 11 calculates a counting rate from the number of pulses and time information exceeding the threshold value, from the AD converters 9D and 10D. The reason for providing the threshold is to remove noise. The counting rate is, for example, the counting number of radiation photons per unit time detected by the detector.

Figure 3:
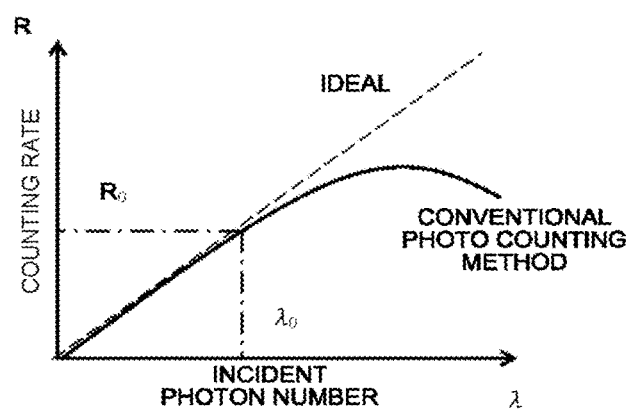
FIG. 3 illustrates a relationship between the number of photons incident on the detection apparatus, an ideal counting rate, and an actual counting rate using a conventional photo counting method.

FIG. 3 illustrates a relationship between the number of radiation photons incident on the detection apparatus, an ideal counting rate, and an actual counting rate using a conventional photon counting method.

In the example of FIG. 3, a dotted line shows a relationship between the number of radiation photons incident on the detection device and the ideal counting rate. A solid line shows a relationship between the number of photons incident on the detection apparatus and the actual counting rate using the conventional photon counting method.

The ideal counting rate shows linearity in which the relationship between the number of radiation photons incident on the detection apparatus and the counting rate is high.

As illustrated in FIG. 3, the relationship between the number of radiation photons incident on the detection apparatus and the actual counting rate using the conventional photon counting method at a low dose shows linearity similarly to the relationship between the number of radiation photons incident on the detection device and the ideal counting rate. However, as compared with the relationship using the ideal counting rate, in the relationship using the actual counting rate using the conventional photon counting method, as the radiation dose becomes higher, the counting rate cannot be measured accurately due to the pile-up of the pulse signals. Therefore, in the case of high doses, the relationship between the number of radiation photons incident on the detection apparatus and the ideal counting rate cannot maintain linearity. For example, the linearity cannot be maintained from the vicinity of an incident radiation photon number ho and the counting rate $R_0$. Therefore, the control method for solving this problem will be described below.

Figure 4:
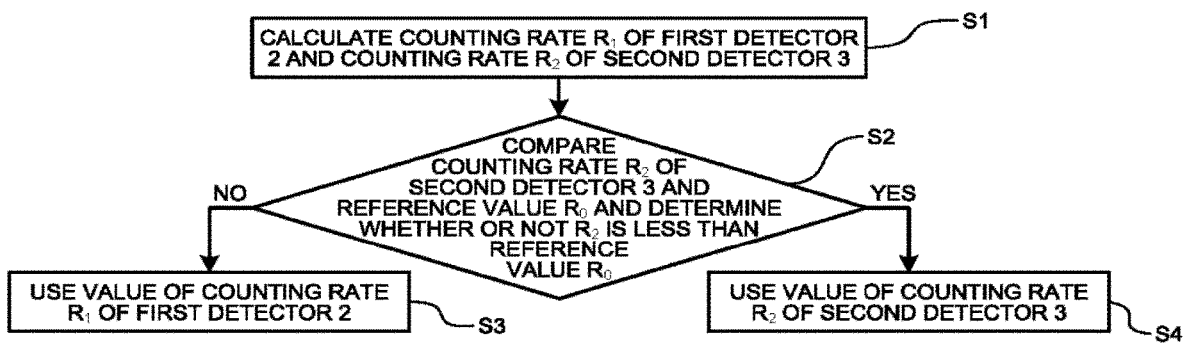
FIG. 4 is a flowchart for explaining a processing procedure in a processing unit.

FIG. 4 is a flowchart for explaining the control method of the processing unit 11.

The processing unit 11 calculates a counting rate $R_1$ of the first detector 2 and a counting rate $R_2$ of the second detector 3 (step S1).

Since in $R_0$, linearity can be maintained in the relationship of the actual counting rate using the conventional photon counting method, the processing unit 11 compares a reference value $R_0$ and the counting rate $R_2$ of the second detector 3 and determines whether or not the counting rate $R_2$ is less than the reference value $R_0$ (step S2). The incident radiation photon number shows the number of radiation photons incident on the detection apparatus.

When the counting rate $R_2$ is equal to or greater than the reference value $R_0$, the processing unit 11 uses the value of the counting rate $R_1$ (step S3).

When the counting rate $R_2$ is less than the reference value $R_0$, the processing unit 11 uses the value of the counting rate $R_2$ (step S4).

Incidentally, in step S3, determination is made using the counting rate $R_2$ of the second detector 3, but it is also possible to compare the counting rate $R_1$ of the first detector 2 with the reference value $R_0'$. Furthermore, in step S3, when the counting rate $R_2$ is larger than the reference value $R_0$, the processing unit 11 uses the value of the counting rate $R_1$. In step S4, when the counting rate $R_2$ is equal to or less than the reference value $R_0$, the processing unit 11 may use the value of the counting rate $R_2$.

Figure 5:
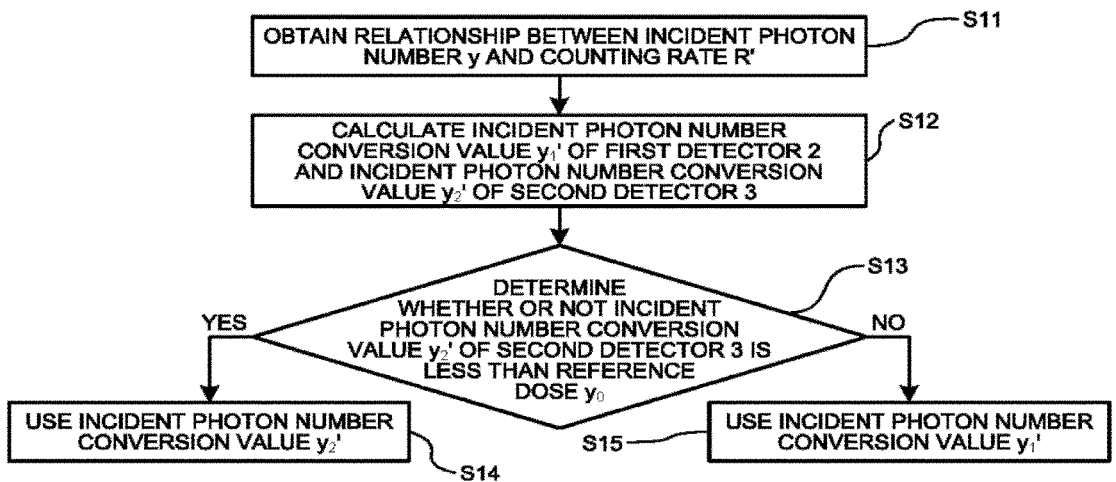
FIG. 5 is a flowchart for explaining a processing procedure in the processing unit.

FIG. 5 is a flowchart for explaining another control method of the processing unit 11.

The processing unit 11 obtains the relationship between an incident radiation photon number y of the first detector 2 and the second detector 3 and a counting rate R' (step S11). Step S11 is a step of calculating conversion coefficients $a_1$ and $a_2$ for estimating the number of radiation photons incident on the detection apparatus. When the counting rate $R_1'$ of the first detector 2 is obtained, the relationship of $y_1 = a_1 R_1'$ is established between the counting rate $R_1'$ and the actual incident radiation photon number $y_1$. Likewise, at the counting rate $R_2'$ of the second detector 3, the relationship of $y_2 = a_2 R_2'$ is established between the counting rate $R_2'$ and the incident radiation photon number $y_2$. If the conversion coefficients $a_1$ and $a_2$ are calculated, the incident radiation photon number y can be estimated from the counting rate R'. Here, since the incident radiation photon number is a converted value, it is shown as an incident radiation photon number conversion value y'.

Next, the counting rate $R_1'$ of the first detector 2 and the counting rate $R_2'$ of the second detector 3 are measured, and the processing unit 11 estimates the incident radiation photon number conversion value $y_1'$ of the first detector 2 and the incident radiation photon number conversion value $y_2'$ of the second detector 3 (step S12).

The processing unit 11 determines whether or not the incident radiation photon number conversion value $y_2'$ of the second detector 3 is less than a reference dose $y_0$ (step S13).

When the incident radiation photon number conversion value $y_2'$ of the second detector 3 is less than the reference dose $y_0$, the processing unit 11 uses the incident radiation photon number conversion value $y_2'$ (step S14). Here, the reference dose $y_0$ is calculated from the reference value $R_0$.

When the incident radiation photon number conversion value $y_2'$ of the second detector 3 is equal to or more than the reference dose $y_0$, the processing unit 11 considers that there is a possibility that the detection apparatus has entered the pile-up state, and uses the incident radiation photon number conversion value $y_1'$ of the first detector 2 (step S15).

As described above, it is controlled which one of electric signals from the first detector 2 and the second detector 3 is used.

Figure 6:
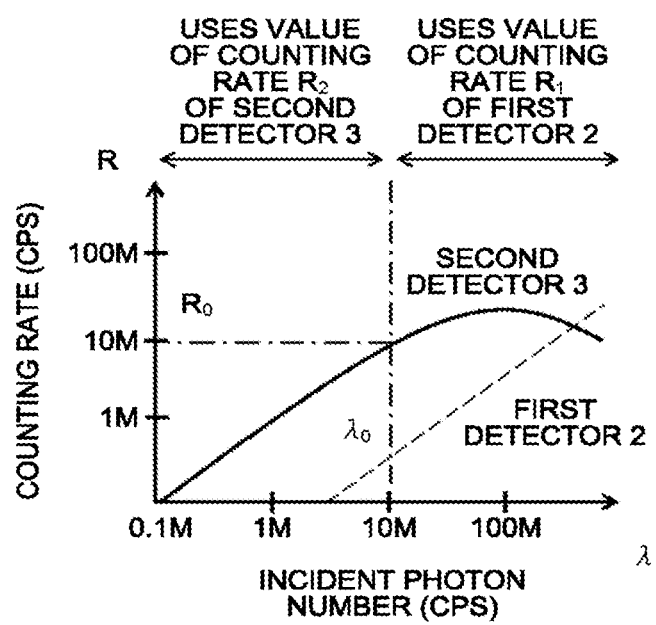
FIG. 6 illustrates a relationship between counting rate and photons incident on the detection apparatus.

FIG. 6 illustrates a relationship between counting rate and the number of radiation photons incident on the detection apparatus.

In the example of FIG. 6, a dotted line shows a relationship between the counting rate using one first detector 2 and the number of radiation photons incident on the detection apparatus. A solid line shows a relationship between the counting rate using about 4000 second detectors 3 around the first detector 2 and the number of radiation photons incident on the detection apparatus. In other words, the counting rates $R_1$ and $R_2$ used for the incident radiation photon number are shown. Further, it is assumed that the light receiving areas of the first detector 2 and the second detector 3 are the same.

The relationship between the counting rate using the second detector 3 and the number of radiation photons incident on the detection apparatus can be measured with high linearity until the number of incident radiation photons is about 10 Mcps. However, at 10 Mcps or later, the counting rate cannot be measured accurately due to the pile-up of pulse signals. cps indicates the number of counts per second.

On the other hand, in the relationship between the counting rate using one first detector 2 and the number of radiation photons incident on the detection apparatus shows that the counting rate can be accurately measured even at a high counting rate of 10 Mcps or more with respect to the number of radiation photons incident on the detection apparatus.

The concept that the counting rate of the first detector 2 can be accurately measured at a high counting rate will be described below.

For example, in the first detector 2 and the second detector 3, when radiation having an average energy e is incident on the scintillator, if the visible light detection amount per unit radiation energy (keV) is n (photon/keV), the number of photons generated inside the scintillator can be given by εη. Assuming that the total number of the first detector 2 and the second detector 3 is $N_{SiPM}$ and the incident frequency of photons is h, when the light receiving areas of the first detector 2 and the second detector 3 are the same, the counting rate $r_{MicroCell}$ detected per one detector can be approximated as shown in expression (1).

$$r_{MicroCell} = \frac{\varepsilon \times \eta \times h}{N_{SiPM}} \quad (1)$$

For example, the average value e of the radiation energy reaching the detector can be 60 keV if a tube bulb voltage of 120 kV is used. In the case of using the LYSO scintillator, since the detection amount of visible light is 2 phonons/keV, when considering the incident of high dose of 100 Mcps as the whole detector, it can be estimated that the counting rate per one detector $r_{MicroCell}$ is 3 Mcps, from expression (1).

In the photon counting technology, since 3 Mcps is smaller than about 10 Mcps which can accurately measure the incident radiation photon number, the linearity of radiation detection can be maintained. That is, although the pile-up occurs with respect to the entire detector, this problem does not arise when looking at a single detector.

Therefore, by properly using the electric signals from the first electrode unit 6 and the second electrode unit 7 according to the counting rate, the detection apparatus of this embodiment can provide a detection apparatus with improved linear detection of radiation detection.

Although the case where the number of the first detectors 2 is one has been described here, the plurality of first detectors 2 may be provided. For example, in the case of the condition described above, since the counting rate $r_{MicroCell}$ per detector is 3 Mcps, the counting rate $r_{MicroCell}$ of the three detectors is 9 Mcps. Since this value is smaller than 10 Mcps, it means that three first detectors 2 may be present. From this, it suffices that the number n of first detectors 2 satisfies the relationship of the expression (2).

$$n \leq \frac{R_0}{r_{MicroCell}} \quad (2)$$

That is, the number of first detectors 2 can be arbitrarily selected according to the counting rate per detector. The number of first detectors is less than the number of second detectors.

Second Embodiment

Only the configuration different from the detection apparatus according to the first embodiment will be described in the detection apparatus according to the second embodiment.

Figure 7A:
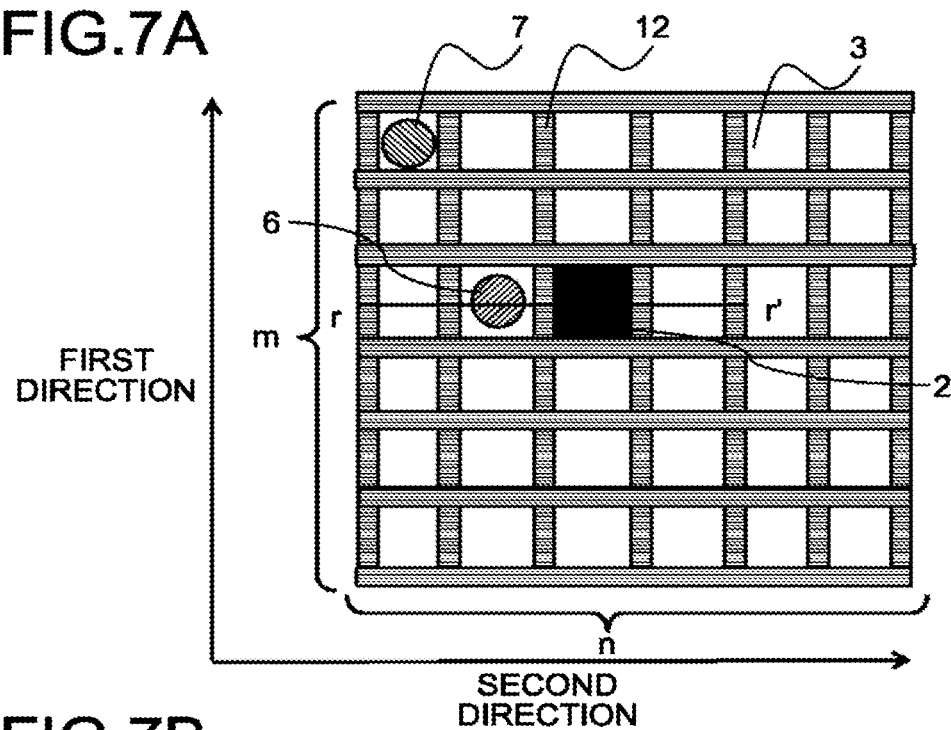
FIGS. 7A and 7B illustrate a detection apparatus according to a second embodiment.

FIG. 7A illustrates the detection apparatus according to this embodiment, and is a plane view of the scintillator 4, the adhesive layer 5, and the second wiring layer 900B, as viewed from the direction of incidence of radiation.

The detection apparatus according to the present embodiment is provided with a separation unit 12 for separating detectors from each other in the detection apparatus according to the first embodiment. The separation unit 12 is provided in an array shape so as to separate the detectors from each other.

Figure 7B:
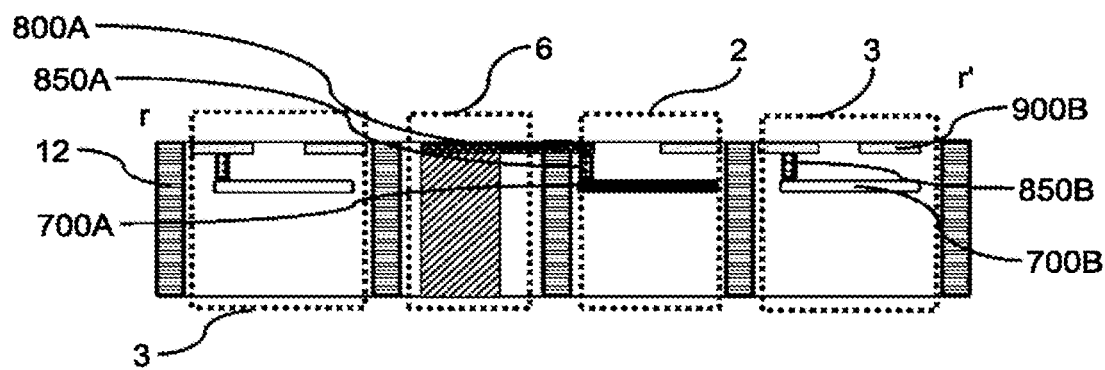

FIG. 7B is a cross-sectional view obtained by cutting r-r' in FIG. 7A along a second direction.

Here, only different points from FIG. 1D will be explained.

The detection apparatus according to the present embodiment is provided with the separation unit 12 that separates detectors from each other. The separation unit 12 has a depth greater than that of the light receiving elements 700A and 700B, as viewed from the direction in which radiation is incident. In the example of FIG. 7B, the separation unit 12 has a size substantially equal to the size of the substrate in the direction in which radiation is incident.

Incidentally, the separation unit 12 is provided to prevent an electric signal from leaking to adjacent detectors by a radiation photon incident on a certain detector. For example, the separation unit 12 may be a separating member or a groove having a function of shielding or dimming light. As the separating member, for example, a metal material such as tungsten, aluminum, copper or the like can be used.

When the detectors are arranged in an array, there is a phenomenon called crosstalk in which light in a wavelength band in the range from visible light to far infrared light is emitted from the detector on which the radiation photon is incident, and this emitted light is incident on the adjacent detector. The frequency of crosstalk occurrence can be reduced by providing the separation unit 12 between the detectors. Therefore, in addition to the effect of the detection apparatus according to the first embodiment, the detection apparatus according to the second embodiment also has the effect of minimizing the influence of crosstalk and the like caused by arranging the detectors in an array as much as possible.

Application Example

An application example of the detection apparatus according to the present embodiment will be described.

The detection apparatuses according to the first embodiment and the second embodiment are staggered with a detection device which outputs an electric signal from one electrode on the light receiving surface to form a plurality of detection devices.

In one of the first direction and the second direction, the detection apparatuses according to the first embodiment and the second embodiment and the detection apparatus for outputting an electric signal from one electrode may be alternately laid.

In the detection apparatus according to the first embodiment and the second embodiment, two types of electric signals are output from the first electrode unit 6 and the second electrode unit 7; therefore, when a group of detection apparatuses is constructed only with the detection apparatuses according to the first embodiment and the second embodiment, the load on the processing system increases because the amount of data increases. Therefore, the detection apparatus adjacent to the detection apparatus according to the first embodiment and adjacent to the detection apparatus according to the second embodiment outputs an electric signal from one electrode, thereby suppressing a net increase in the amount of data.

The detection apparatus according to this embodiment can be introduced into a computer tomography apparatus, a radioactivity measurement apparatus, or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detection apparatus comprising:
   at least one first detector that detects a photon;
   second detectors that detect a photon, a number of the second detectors being more than a number of the at least one first detector; and
   processing circuitry configured to
      receive a first signal from the at least one first detector and a second signal from the second detectors,
      calculate a first counting rate by counting the number of pulses exceeding a first predetermined threshold value from the first signal,
      calculate a second counting rate by counting the number of pulses exceeding a second predetermined threshold value from the second signal, and
      generate output data based on one of the first counting rate and the second counting rate.

2. The detection apparatus according to claim 1, wherein the number n of the at least one first detector is a number satisfying the expression (1), $$r_{MicroCell} = \frac{\varepsilon \times \eta \times h}{N_{SiPM}} \quad (1)$$

where $R_0$ is a predetermined reference value, $r_{MicroCell}$ is a counting rate detected per one detector calculated from expression (2), $$n \leq \frac{R_0}{r_{MicroCell}} \quad (2)$$

where $\varepsilon$ is an average energy of photon, $\eta$ (photon/keV) is a photon detection amount per unit energy (keV), $N_{SiPM}$ is the total number of the first detector and the second detector, and h is an incident frequency of a photon.

3. The detection apparatus according to claim 1, wherein the number of the at least one first detector is one.

4. The detection apparatus according to claim 1, further comprising a scintillator that emits a photon upon incidence of radiation on the at least one first detector and the second detectors.

5. The detection apparatus according to claim 1, further comprising separation circuitry provided between the at least one first detector and one of the second detectors or between the second detectors.

6. The detection apparatus according to claim 1, wherein the at least one first detector and the second detectors have an identical light receiving region.

7. The detection apparatus according to claim 1, wherein the at least one first detector has a light receiving region having a size different from the second detectors.

8. The detection apparatus according to claim 1, further comprising:
   first reading circuitry including a first amplifier that amplifies the first signal, waveform analyzing circuitry configured to analyze a height of a wave of the first signal amplified by the first amplifier, and an analog to digital converter that converts the first signal output from the waveform analyzing circuitry into a digital signal; and
   second reading circuitry including a second amplifier that amplifies the second signal, waveform analyzing circuitry configured to analyze a height of a wave of the second signal amplified by the second amplifier, and an analog to digital converter that converts the second signal output from the waveform analyzing circuitry into a digital signal.

9. The detection apparatus according to claim 1, wherein the processing circuitry generates output data using the second counting rate when the second counting rate is less than a reference rate, and when the second counting rate is larger than the reference rate, generates output data using the first counting rate.

10. A detection method employed in a detection apparatus comprising:
    detecting photons by at least one first detector and second detectors;
    converting the photons detected by the at least one first detector and the second detectors into a first signal and a second signal respectively;
    calculating a first counting rate by counting the number of pulses exceeding a first predetermined threshold value from the first signal;
    calculating a second counting rate by counting the number of pulses exceeding a second predetermined threshold value from the second signal; and
    generating output data based on one of the first counting rate and the second counting rate.

11. The detection method according to claim 10, wherein calculating the first counting rate includes calculating a counting rate $R_1$ of the at least one first detector by counting the number of pulses exceeding the first predetermined threshold value from the first signal, and
    calculating the second counting rate includes calculating a counting rate $R_2$ of the second detectors by counting the number of pulses exceeding the second predetermined threshold value from the second signal, the method further comprising:

comparing $R_2$ with a predetermined reference value $R_0$; and outputting the value of $R_2$ when $R_2$ is less than $R_0$ and outputting a value of $R_1$ when $R_2$ is equal to or greater than $R_0$.

12. The detection apparatus according to claim 9, wherein when the second counting rate is equal to the reference rate, the processing circuitry generates output data using the first counting rate.

13. The detection apparatus according to claim 9, wherein when the second counting rate is equal to the reference rate, the processing circuitry generates output data using the second counting rate.

* * * * *